United States Patent
Roeseler et al.

(12) 
(10) Patent No.: US 6,706,938 B2
(45) Date of Patent: Mar. 16, 2004

(54) ADSORPTIVE SEPARATION PROCESS FOR RECOVERY OF PARA-XYLENE

(75) Inventors: Cara M. Roeseler, Winfield, IL (US); Santi Kulprathipanja, Inverness, IL (US); James E. Rekoske, Glenview, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 10/099,780

(22) Filed: Mar. 15, 2002

(65) Prior Publication Data

US 2002/0103408 A1 Aug. 1, 2002

Related U.S. Application Data

(63) Continuation of application No. 09/713,082, filed on Nov. 16, 2000, now abandoned.

(51) Int. Cl.$^7$ .................................................. C07C 7/12
(52) U.S. Cl. ....................... 585/820; 585/825; 585/827; 585/828
(58) Field of Search ................ 585/820, 825, 585/827, 828

(56) References Cited

U.S. PATENT DOCUMENTS

| | | | |
|---|---|---|---|
| 3,510,423 A | 5/1970 | Neuzil et al. | 208/310 |
| 3,686,342 A | 8/1972 | Neuzil | 260/674 SA |
| 4,006,197 A | 2/1977 | Bieser | 260/676 MS |
| 4,036,745 A | 7/1977 | Broughton | 208/310 Z |
| 4,283,587 A | 8/1981 | Rosback et al. | 585/828 |
| 4,326,092 A | 4/1982 | Neuzil | 585/828 |
| 4,442,222 A | 4/1984 | Smolin et al. | 502/60 |
| 5,382,747 A | 1/1995 | Kulprathipanja | 585/828 |
| 5,849,981 A | 12/1998 | Kulprathipanja | 585/828 |
| 5,948,950 A | 9/1999 | Hotier et al. | 585/828 |

FOREIGN PATENT DOCUMENTS

FR  2 789 914  2/1999 ............ B01J/20/18

OTHER PUBLICATIONS

D.B. Broughton et al. "The Parex Process for Recovering Paraxylene" *Chemical Engineering Progress* (vol. 66, No. 9) Sep. 1970, p. 70–75.

D.B. Broughton et al. "Adsorptive Separations by Simulated Moving Bed Technology: The Sorbex Process" Presented at the International Conference on Fundamentals of Adsorption, Schloss Elmau, Upper Bavaria, West Germany; May 6–11, 1983.

*Primary Examiner*—Walter D. Griffin
*Assistant Examiner*—Tam M. Nguyen
(74) *Attorney, Agent, or Firm*—John G. Tolomei; James C. Paschall; David J. Piasecki

(57) ABSTRACT

The performance of an adsorptive separation process recovering para-xylene from a $C_8$ aromatic hydrocarbon feed mixture is improved by operating the process at higher desorbent purity. The improved performance allows for tradeoffs in other operating parameters and rates or improved product rates. The process preferably employs a barium and potassium exchanged zeolitic molecular sieve as the adsorbent and toluene as the desorbent.

5 Claims, No Drawings

ADSORPTIVE SEPARATION PROCESS FOR RECOVERY OF PARA-XYLENE

CROSS-REFERENCE TO RELATED APPLICATION

This application is a Continuation of U.S. application Ser. No. 09/713,082 which was filed on Nov. 16, 2000, now abandoned.

FIELD OF THE INVENTION

The invention relates to a process for the adsorptive separation of a xylene, preferably para-xylene, from a feed stream containing an admixture of $C_8$ aromatic hydrocarbons. More specifically the invention relates to improving the performance of a simulated moving bed liquid-phase adsorptive separation process for the recovery of para-xylene from other $C_8$ aromatic hydrocarbons.

RELATED ART

Simulated moving bed (SMB) technology is used commercially in a number of large scale petrochemical separations. The general technique employed in the performance of a simulated moving bed adsorptive separation is well described in the open literature. For instance a general description directed to the recovery of para-xylene was presented at page 70 of the September 1970 edition of *Chemical Engineering Progress* (Vol. 66, No 9). A generalized description of the process with an emphasis on mathematical modeling was given at the International Conference on "Fundamentals of Adsorption", Schloss Elmau, Upper Bavaria, Germany on May 6–11, 1983, by D. B. Broughton and S. A. Gembicki. Numerous other available references describe many of the mechanical parts of a simulated moving bed system, including rotary valves for distributing various liquid flows, the internals of the adsorbent chambers and control systems.

U.S. Pat. No. 3,686,342 issued to R. W. Neuzil describes the separation of para-xylene from mixed xylenes using simulated countercurrent adsorption employing a zeolitic adsorbent and para diethylbenzene as the desorbent. This combination is a good representation of a commercial operation for this particular separation.

U.S. Pat. No. 3,510,423 to R. W. Neuzil et al. provides a depiction of the customary manner of handling the raffinate and extract streams removed from an SMB process, with the desorbent being recovered from each of these streams by fractional distillation, combined and recycled to the adsorption zone. U.S. Pat. No. 4,006,197 to H. J. Bieser extends this teaching on desorbent recycling to three component desorbent mixtures. U.S. Pat. No. 4,036,745 describes the use of dual desorbents with a single adsorption zone to provide a higher purity paraffin extract.

U.S. Pat. No. 5,948,950 issued to G. Hotier et al describes a process for separating para-xylene from a $C_8$ feed in a simulated moving bed process using a zeolitic adsorbent and a desorbent, which can be toluene. The patent stresses the importance of proper hydration of the zeolite to good separation performance, with the hydration level being maintained by water injection into one of the process streams circulating through the adsorbent. The desorbent to feed ratio (S/F) disclosed in this reference varies from 0.6 to 2.5. The reference describes the use of several molecular sieve based adsorbents including barium and potassium exchanged X and Y zeolites. The performance of the process is measured in terms of a performance index designated IP.

This reference, like the others cited above, is silent as to the importance of desorbent purity to the performance of the overall process.

BRIEF SUMMARY OF THE INVENTION

The invention is an adsorptive separation process for the recovery of para xylene from a mixture of $C_8$ aromatic hydrocarbons. The process is operated at conditions, including high desorbent purity, providing improved overall performance at the same volumetric ratio of desorbent to feed (D/F). The invention allows the D/F ratio to be more widely varied depending on feed composition, target performance levels and desired adsorption zone operating temperature.

The invention may be characterized as a simulated moving bed adsorptive separation process for the separation of para-xylene from a feed mixture comprising at least one other $C_8$ aromatic in which the feed mixture is contacted with a zeolitic molecular sieve, which sieve has been exchanged with at least barium, at adsorption promoting conditions including a temperature ranging from 210–300° F., para xylene is selectively adsorbed on the molecular sieve and subsequently removed using a desorbent stream comprising toluene, characterized by maintaining a performance index above 90 at an A/F ratio of from about 0.5 to about 0.7 by operating with a toluene purity in the adsorbent above 98 vol. % allowing operation at an $L_3/A$ ratio of about 1.6 to about 2.3, where A=rate of simulated circulation of selective pore volume through the process, F=volumetric feed rate of the feed mixture, $L_3$=liquid flow rate through zone 3 and IP=square root of (yield % times purity %) of para xylene in the extract product stream of the process.

DESCRIPTION AND PREFERRED EMBODIMENTS

The polyester fabrics and articles which are in wide use today are produced from a polymer of ethylene glycol and teraphthalic acid. Teraphthalic acid is produced by the oxidation of para-xylene. Para-xylene is thus an important raw material in the polyester and chemical industries. Para-xylene is typically recovered from a predominantly $C_8$ aromatic hydrocarbon fraction which is derived from various sources of aromatic hydrocarbons, such as catalytic reforming, by liquid-liquid extraction and/or fractional distillation. The para-xylene is commercially separated from a para-xylene containing feed stream, usually containing all three xylene isomers, by either crystallization or adsorptive separation or a combination of these two techniques. Adsorptive separation is the newer technique and has captured a great majority of the market share of newly constructed plants for the production of para-xylene.

Essentially all of the commercial adsorptive separation units for the recovery of para-xylene use a simulated countercurrent movement of the adsorbent and the xylene containing feed stream due to superior performance compared to swing bed adsorption. This simulation of adsorbent movement is performed using established commercial technology wherein beds of the adsorbent are held in place in one or more cylindrical adsorbent chambers and the positions at which the streams involved in the process enter and leave the chambers are slowly shifted along the length of the beds. Normally there are at least four streams (feed, desorbent, extract and raffinate) employed in this procedure and the location at which the feed and desorbent streams enter the chamber via individual bedlines and the extract and raffinate streams leave the chamber via other bedlines are simultaneous shifted in the same direction at set intervals. Each shift in location of these transfer points delivers or removes liquid from a different bed within the adsorbent chamber. This shifting could be performed using a dedicated bedline for each stream at the entrance to each bed. However, a large scale SMB process unit will normally have at least 8 separate beds, with many of the commercial units having 24 separate beds. Employing a separate bedline for each stream at each bed would greatly increase the cost of the process and therefore the bedlines are reused with each bedline carrying one of the four process streams at some point in the cycle. This is a highly simplified description of the SMB process.

As described in the references cited above, an SMB process produces at least two effluent streams; an extract stream containing a compound which was selectively retained on the adsorbent and a raffinate stream containing compound(s) which were not adsorbed. Both the extract and the raffinate streams will also contain the desorbent compound(s). The concentration of the desorbent in the extract and raffinate stream will vary somewhat with time during each incremental shifting of the process bed lines due several factors. The extract and raffinate streams are passed into fractionation columns, referred to in the art as the extract and raffinate columns, in which the desorbent is separated from the extract and raffinate compounds. The desorbent is in this way recovered, and it is then recirculated to the adsorption zone as a process stream referred to herein as the desorbent stream.

In the practice of the present invention, a feed mixture comprising two or more classes of hydrocarbons such as hydrocarbons of different skeletal structure and also other different hydrocarbons is passed through one or more beds of an adsorbent which selectively adsorbs desired paraffins of one class (skeletal structure) while permitting other components of the feed stream to pass through the adsorption zone in an unchanged condition and become part of a raffinate stream. The flow of the feed through the adsorbent bed is stopped and the adsorption zone is then flushed to remove nonadsorbed materials surrounding the adsorbent. Thereafter the adsorbed hydrocarbon is desorbed from the adsorbent by passing a desorbent stream through the adsorbent bed forming an extract stream. The desorbent material is commonly also used to flush nonadsorbed materials from the void spaces around and within the adsorbent. Both the raffinate and extract stream contain the desorbent compound (s) and are fractionated to recover the desorbent.

Numerous reasons exist as to why, during the recovery of a xylene, the separation being performed in the extract or raffinate column may results in undesirably high levels of $C_8$ aromatic hydrocarbons being present in the desorbent stream. First, the initial design of these columns may have been made with a desire to minimize capital or operating costs and without recognition of the importance of desorbent stream purity on unit performance. A second reason is that the separation capacity of the extract and raffinate columns can become taxed when the feed rate to these columns is increased due to an increase in the adsorption unit feed rate. It may be possible to address this problem to some extent by changes in the internal structure of the column e.g. by the installation of higher capacity trays or by changes in the operation of the column. But such changes can only provide a limited amount of increased fractionation capacity. At this point the performance of the columns will begin degrade with increased column feed rates. Such increases in the feed rate to the extract and raffinate column can occur due to an increase in the rate at which the feed is being charged to an existing adsorption chamber(s) or by an increase in the size of the chambers which allows operation at a higher feedstock charge rate. It is also possible that the throughput of the adsorption zone will be increased to due the installation of an improved adsorbent or an improvement in some operational aspect of the adsorption zone such as improved controls on the shifting of the zones in the chambers, use of different flush streams or different flush methods, etc. All of these factors can occur during the revamping or debottlenecking of the adsorption portion of the separation unit.

It is an objective of this invention to provide an adsorptive separation process for the recovery of para xylene from a $C_8$ aromatic hydrocarbon feed mixture. It is a further objective of the subject process to provide a simulated moving bed adsorptive separation process which allows optimum utilization of existing fractional distillation columns used for desorbent recovery after an expansion of the adsorption zone or a significant increase in the feed rate to the overall process. It is a specific objective of the invention to optimize the performance of a toluene-desorbent based adsorptive separation process for the production of para xylene.

It has been discovered that the purity of the desorbent stream returned from the extract and raffinate columns has a significant effect on the performance of the adsorption zone. As used herein purity is measured in terms of the volumetric amount of toluene or other desorbent compound(s) present in the desorbent stream delivered to the flow distribution device e.g. rotary valve of the adsorption chamber. The main expected impurities will be $C_8$ aromatic hydrocarbons such as ethylbenzene or xylenes present in the feed stream. The use of a desorbent stream containing less than 1000 ppm $C_8$ aromatic hydrocarbons is preferred. A concentration of $C_8$ aromatic hydrocarbons in the desorbent stream of only 2000 ppm has a marked effect on the performance of the process and is a relative high level of impurity for the desorbent. It has also been discovered that by operation in a relatively narrow range of conditions of temperature and flows the performance of the separation, as measured by an IP index, can be maintained at a high level by maintaining an $L_3/A$ ratio above 1.95. The desorbent is normally referred to herein in the singular, but the desorbent could be formed by two or more compounds if such a two component system is desired.

While this description primarily addresses the recovery of a xylene, the importance of desorbent purity should extend to other SMB process applications in which raffinate components may come to contaminate the desorbent. Such applications include the recovery of normal paraffins or olefins from mixed acyclic hydrocarbons.

It is preferred to operate the adsorption zone at conditions which include a temperature below 177° C. (350° C.) as this provides better selectivity and capacity. It is especially preferred to operate in the temperature range of 210–300° F. (99–149° C.). A temperature of about 250–275° F. (121–135°) is highly preferred. Another important operational variable is the water content of the sieve. This variable is described for instance in the Hotier reference cited above and other references such as U.S. Pat. No. 3,734,974. As a commercial process operates continuously with the adsorbent confined within the chambers the acknowledged method of operation includes adding water, as required, to feed stream. The level of hydration of the adsorbent is reported on a volatile free basis or by a measurement referred to as Loss on Ignition(LOI) as described in U.S. Pat. No. 5,900,523. In the LOI test the volatile matter content of the zeolitic adsorbent is determined by the weight difference obtained before and after drying a sample of the adsorbent at 500° C. under an inert gas purge such as nitrogen for a period of time sufficient to achieve a constant weight. A higher LOI is often desired at higher operating temperatures. A hydration level giving an LOI of about 2.8–4.0 is preferred with an adsorbent containing an X zeolite. Other operating variables include the $L_3/A$ ratio and the A/F ratio as defined herein. The A/F ratio sets an operating curve, specific to a particular $L_3$ rate. Operating with an A/F ratio of about 0.5 to about 0.7 is preferred. A process unit designed for normally producing a high purity product (e.g. 99%) will operate at the higher end of this general range. Units designed to produce low purity product of 80–85% purity for feeding to a crystallizer will operate in the lower portion of this range. The operating conditions interact such that overall optimum performance requires balancing the effects of several conditions. As an example of variable interplay, increasing the $L_3/A$ ratio increases recovery but requires more desorbent circulation. It is to be noted that it is normally preferred to minimize both $L_3$ and A, which leads to a need to balance initial design and operations. Operating at an $L_3/A$ ratio of from about 1.6 to about 2.3 is preferred. The D/F ratio can be varied based upon feed composition, target recovery and purity, sieve hydration level and operating temperature. Desorbent purity is now added to this list of operating variables.

The invention may be characterized as a simulated moving bed adsorptive separation process for the separation of para-xylene from a feed mixture comprising at least one other $C_8$ aromatic in which the feed mixture is contacted with a zeolitic molecular sieve, which sieve has been exchanged with at least barium, at adsorption promoting conditions including a temperature ranging from 210–300° F., para xylene is selectively adsorbed on the molecular sieve and subsequently removed using a desorbent stream comprising toluene, characterized by maintaining a performance index above 90 at an A/F ratio less than 0.7 by operating with a toluene purity in the adsorbent above 98 vol. % allowing operation at an $L_3/A$ ratio greater than 1.95.

The adsorption and desorption steps can be performed in a single large bed of adsorbent or in several parallel beds on a swing bed basis. However, it has been found that simulated moving bed adsorptive separation provides several advantages such as high purity and recovery. Therefore, many commercial scale petrochemical separations, especially those for the separation of xylenes and mixed normal paraffins are performed using simulated countercurrent moving bed (SMB) technology. The previously sited references are incorporated for their teaching on the performance of this technique. Further details on equipment and techniques for using in an SMB process may be found in U.S. Pat. Nos. 3,208,833; 3,214,247; 3,392,113; 3,455,815; 3,523,762; 3,617,504; 4,006,197; 4,133,842; and 4,434,051. A different type of simulated moving bed operation which can be performed using similar equipment, adsorbent and conditions but which simulates cocurrent flow of the adsorbent and liquid in the adsorption chambers is described in U.S. Pat. Nos. 4,402,832 and 4,498,991.

The adsorbent chamber(s) of the adsorption zone and other portions of the process can be operated at conventional conditions using otherwise standard equipment. The process also employs a conventional adsorbent-desorbent system. The adsorbent is linked with the desorbent as the performance of the overall process is dependent on both and they are not normally interchangeable. That is, a desorbent which functions well with one adsorbent will not necessarily give good results when used with a different adsorbent. The preferred adsorbents for the subject process are based upon zeolitic molecular sieves, with X and Y zeolites being preferred and with an adsorbent containing an X zeolite being especially preferred. It is known in the art that ion exchange of the zeolite with different cations will change its adsorption characteristics. For the separation of para xylene from $C_8$ aromatics it is preferred to exchange the zeolite with barium and/or potassium. The use of a barium exchanged zeolite containing 20 to 29 percent barium is especially preferred. Another highly preferred adsorbent comprises an X zeolite which has been ion exchanged to contain both barium and potassium. Further information on adsorbents is available in the patent literature.

The preferred desorbent used in the subject process is toluene. The invention is believed to be generally applicable to other desorbents including para diethyl benzene. The choice of an adsorbent-desorbent system is normally governed by economic factors which in turn are controlled by performance of the adsorbent-desorbent pair in terms of recovery and purity at specific conditions and for specific feed compositions. Therefore, most preferences expressed herein are determined by technology factors such as adsorbent capability and economic factors such as the desired product and its purity. These preferences will vary with the economic and business situation of specific units.

As mentioned above the desire to minimize the operating and capital cost of the overall process can lead to operation of the extract and desorbent columns at conditions which result in the presence of a greater amount of $C_8$ aromatics than a new column would normally be designed for. Or the initial design of a unit may be premised on the concept that only a reasonably good separation is needed since the product of the separation is only an internally recycled stream. It has been determined, however, that the purity of the desorbent is a separate and sensitive variable in its own right much the same as the hydration of the molecular sieve or the operating temperature. This factor has not been previously discussed in the art.

The importance of desorbent purity is illustrated by the following example based upon actual small scale testing involving the separation of para xylene from a mixture of ortho, meta and para xylenes and ethylbenzene. The tests were conducted at 125° C. (257° F.) under liquid phase conditions employing toluene as a desorbent and a barium and potassium exchanged X zeolite. The tests were performed at an adsorbent to feed ratio (A/F) of 0.5 and an $L_3/A$ ratio of 1.98. With an essentially pure desorbent stream the para xylene recovery from the feed was 95.6 vol. % with a 95.0% purity. When the desorbent contained 2000 ppm of the raffinate materials (all the feed components including para xylene) the para xylene recovery dropped to 95.0 vol. % with the purity to 95%. While this may not seem like a big change, it is pointed out the change in recovery was three times the change in the desorbent purity.

The invention may accordingly be characterized as an adsorptive separation process to recover a xylene from a feed stream comprising at least two xylenes, which process comprises passing a feed stream comprising at least a first and a second xylene into an adsorptive separation zone, which zone is maintained at adsorptive separation promoting conditions including a temperature of 210–300° F., and contacting the feed stream with a selective adsorbent, selectively retaining the first xylene in the selective adsorbent, and recovering from the adsorptive separation zone a raffinate stream comprising a desorbent and the second xylene, which is not selectively retained on the selective adsorbent;

passing a desorbent stream comprising at least 99 vol. % desorbent compound into the adsorptive separation zone and into contact with the selective adsorbent under desorption promoting conditions and producing an extract stream comprising the desorbent and the first xylene; fractionating the extract and raffinate streams to recover the desorbent compound and producing an extract product stream, a raffinate product stream and a recovered desorbent stream; and passing at least a portion of the desorbent stream into the adsorptive separation zone.

Feed mixtures which can be charged to the process of this invention are those which are normally charged to an conventional adsorptive separation process. Typical feed streams will contain a mixture of all three xylene isomers plus ethylbenzene. The relative concentration of the three xylenes in the feed stream can vary significantly. The feed stream may be produced by liquid extraction of aromatic hydrocarbons from a naphtha boiling range reformate followed by fractional distillation to isolate $C_8$ aromatics. The feed may also be produced by a xylene isomerization zone or by a transalkylation process or a toluene disproportionation process. Often the raffinate compounds rejected from the subject separation are recycled to an isomerization zone in which more of the desired xylene is produced. Thus the adsorptive separation and isomerization zones may form a loop in which feed xylenes are converted and separated to one single xylene.

The subject adsorptive separation process can be used to produce a high purity xylene product stream (greater than 99.5% pure) or a lower purity xylene of e.g. 85% xylene. The lower purity may be suitable as a solvent or may be passed into a subsequent separation zone for the production of a higher purity final product. For instance, the xylene product stream of the subject process could be passed into a crystallization zone for the ultimate recovery of a high purity xylene stream.

The preferred product of the subject process is para xylene. However, the process is not so limited and with a properly chosen adsorbent/desorbent system and suitable operating conditions other xylenes could be the product. For instance, there is significant interest in the recovery of meta xylene. Information on adsorbents and operation conditions for the recovery of meta xylene may be obtained by reference to U.S. Pat. No. 3,840,610; 4,306,107; 4,326,092; 4,571,441 and 5,382,747 which are incorporated for this teaching.

Operating conditions may be set by several considerations. For instance, there is often a tradeoff between higher recovery at higher temperatures and higher purity at lower temperatures. Adsorption promoting conditions also include a pressure sufficient to maintain the process fluids in liquid phase; which may be from about atmospheric to 600 psig. Desorption conditions generally include the same temperatures and pressure as used for adsorption conditions. The practice of the subject invention requires no significant variation in operating conditions, adsorbent or desorbent composition within the adsorbent chambers. That is, the adsorbent in a chamber preferably remains at the same temperature throughout the process.

The A/F ratio is a separate design variable which greatly effect the performance of the process and the cost of the process unit. As A relates directly to the quantity of adsorbent retained in the adsorbent chambers, a high A/F ratio leads directly to the need for a larger unit to accommodate the adsorbent. The cost of the adsorbent itself also increases. Therefore it is desired to operate at a minimum acceptable A/F ratio.

Another ratio which should be minimized is the $L_3/A$ ratio, where $L_3$ represents the net liquid flow rate through the adsorption zone. As the flow of the feed stream is set, $L_3$ can basically be varied only by varying the flow rate of the desorbent. Minimizing this flow reduces required fluid flows which allows for smaller transfer lines and reduced size and operating costs for the extract and raffinate columns.

Performance, measured by both selectivity and capacity, varies greatly between different adsorbent/desorbent systems. It is affected by feed composition, operating temperature and sieve hydration. It has now been determined that solvent purity has a significant impact on overall process performance and must also be considered along with these other factors during process design and operation.

The active component of the adsorbents is normally used in the form of particulate agglomerates having higher physical strength and attrition resistance than the active components themselves. The agglomerates contain the active adsorptive material dispersed in an amorphous, inorganic matrix or binder, having channels and cavities therein which enable fluid to access the adsorptive material. Methods for forming the crystalline powders into such agglomerates include the addition of an inorganic binder, generally a clay comprising a silicon dioxide and aluminum oxide, to a high purity adsorbent powder in a wet mixture. The binder aids in forming or agglomerating the crystalline particles. The blended clay-adsorbent mixture may be extruded into cylindrical pellets or formed into beads which are subsequently calcined in order to convert the clay to an amorphous binder of considerable mechanical strength. The adsorbent may also be bound into irregular shaped particles formed by spray drying or crushing of larger masses followed by size screening. The adsorbent particles may thus be in the form of extrudates, tablets, spheres or granules having a desired particle range, preferably from about 16 to about 60 mesh (Standard U.S. Mesh) (1.9 mm to 250 microns). Clays of the kaolin type, water permeable organic polymers or silica as appropriate are generally used as binders.

The active molecular sieve component of the adsorbents will ordinarily be in the form of small crystals present in the adsorbent particles in amounts ranging from about 75 to about 98-wt. % of the particle based on volatile-free composition. Volatile-free compositions are generally determined after the adsorbent has been calcined at 900° C. in order to drive off all volatile matter. The remainder of the adsorbent will normally be the inorganic matrix of the binder present in intimate mixture with the small particles of the adsorbent material. This matrix material may be an adjunct of the manufacturing process for the silicalite, for example, from the intentionally incomplete purification of the silicalite during its manufacture.

An important characteristic of an adsorbent is the rate of exchange of the desorbent for the extract component of the feed mixture materials or, in other words, the relative rate of desorption of the extract component. This characteristic relates directly to the amount of desorbent material that must be employed in the process to recover the extract component from the adsorbent. Faster rates of exchange reduce the amount of desorbent material needed to remove the extract component, and therefore, permit a reduction in the operating cost of the process. With faster rates of exchange, less desorbent material has to be pumped through the process and separated from the extract stream for reuse in the process. Exchange rates are often temperature dependent. Ideally, desorbent materials should have a selectivity equal to about 1 or slightly less than 1 with respect to all extract components so that all of the extract components can be desorbed as a class with reasonable flow rates of desorbent material, and so that extract components can later displace desorbent material in a subsequent adsorption step.

In adsorptive separation processes, which are generally operated continuously at substantially constant pressures and a temperature which insures liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity, it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the capacity of the adsorbent or selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent void volume in admixture with desorbent material and any chemical reaction involving a desorbent material and an extract component or a raffinate component or both would complicate or prevent product recovery. The desorbent should also be easily separated from the extract and raffinate components, as by fractionation. Finally, desorbent materials should be readily available and reasonable in cost.

For purposes of this description of the invention various terms are defined as follows. A "feed mixture" is a mixture containing one or more extract components and one or more raffinate components to be separated by the process. The term "feed stream" indicates a stream of a feed mixture which is passed into contact with the adsorbent used in the process. An "extract component" is a compound or class of compounds that is more selectively adsorbed by the adsorbent while a "raffinate component" is a compound or type of compound that is less selectively adsorbed. The term "desorbent compound" means generally a material capable of desorbing an extract component from the adsorbent. The term "raffinate stream" or "raffinate output stream" means a stream in which a raffinate component is removed from the adsorbent bed after the adsorption of extract compounds. The composition of the raffinate stream can vary from essentially 100% desorbent material to essentially 100% raffinate components. The term "extract stream" or "extract output stream" means a stream in which an extract material, which has been desorbed by a desorbent material, is removed from the adsorbent bed. The composition of the extract stream can vary from essentially 100% desorbent material to essentially 100% extract components.

At least portions of the extract stream and the raffinate stream are passed to separation means, typically fractional distillation columns, where at least a portion of desorbent material is recovered and an extract product and a raffinate product are produced. The terms "extract product" and "raffinate product" mean streams produced by the process containing, respectively, an extract component and a raffinate component in higher concentrations than those found in the extract stream and the raffinate stream withdrawn from adsorbent chamber. The extract stream may be rich in the desired compound or may only contain an increased concentration. The term "rich" is intended to indicate a concentration of the indicated compound or class of compounds greater than 50 mole percent.

It has become customary in the art to group the numerous beds in the SMB adsorption chamber(s) into a number of zones. Usually the process is described in terms of 4 or 5 zones. First contact between the feed stream and the adsorbent is made in Zone I, the adsorption zone. The adsorbent or stationary phase in Zone I becomes surrounded by liquid which contains the undesired isomer(s), that is, with raffinate. This liquid is removed from the adsorbent in Zone II, referred to as a purification zone. In the purification zone the undesired raffinate components are flushed from the void volume of the adsorbent bed by a material which is easily separated from the desired component by fractional distillation. In Zone III of the adsorbent chamber(s) the desired isomer is released from the adsorbent by exposing and flushing the adsorbent with the desorbent (mobile phase). The released desired isomer and accompanying desorbent are removed from the adsorbent in the form of the extract stream. Zone IV is a portion of the adsorbent located between Zones I and III which is used to segregate Zones I and III. In Zone IV desorbent is partially removed from the adsorbent by a flowing mixture of desorbent and undesired components of the feed stream. The liquid flow through Zone IV prevents contamination of Zone III by Zone I liquid by flow cocurrent to the simulated motion of the adsorbent from Zone III toward Zone I. A more thorough explanation of simulated moving bed processes is given in the Adsorptive Separation section of the Kirk-Othmer Encyclopedia of Chemical Technology at page 563. The terms "upstream" and "downstream" are used herein in their normal sense and are interpreted based upon the overall direction in which liquid is flowing in the adsorbent chamber. That is, if liquid is generally flowing downward through a vertical adsorbent chamber, then upstream is equivalent to an upward or higher location in the chamber.

What is claimed:

1. In a simulated moving bed adsorptive separation process for the separation of para-xylene from a feed mixture comprising other $C_8$ aromatics, in which process the feed mixture is contacted with a zeolitic molecular sieve, which sieve has been exchanged with at least barium, at adsorption promoting conditions including a temperature ranging from 210–300° F., para xylene is selectively adsorbed on the molecular sieve and subsequently removed using a desorbent stream comprising toluene, the improvement which comprises maintaining a performance index (IP) above 90 at an A/F ratio of from about 0.5 to about 0.7 by operating with a desorbent stream purity above 98 vol. % allowing operation at an $L_3$/A ratio of about 1.6 to about 2.3 where A=rate of simulated circulation of selective pore volume through the process, F=volumetric feed rate of the feed mixture, $L_3$=liquid flow rate through zone 3, and IP=square root of (yield % times purity %) of para xylene in the extract product stream of the process.

2. The invention of claim 1 wherein the volumetric ratio of desorbent to feed is maintained less than 1.2.

3. The invention of claim 1 wherein the total concentration of $C_8$ aromatic impurities in the desorbent stream is less than 2,000 ppm.

4. The invention of claim 1 wherein the total concentration of $C_8$ aromatic impurities in the desorbent stream is less than 1,000 ppm.

5. The process of claim 1 wherein the molecular sieve has been exchanged with both barium and potassium.

* * * * *